(12) United States Patent
Dennis et al.

(10) Patent No.: US 8,029,432 B2
(45) Date of Patent: Oct. 4, 2011

(54) MAGNETIC SYSTEM FOR TREATMENT OF CELLULAR DYSFUNCTION OF A TISSUE OR AN EXTRACELLULAR MATRIX DISRUPTION OF A TISSUE

(75) Inventors: Robert Glenn Dennis, Chapel Hill, NC (US); Paul Edward Kosnik, Jonestown, TX (US); James Ronald Clark, Kingwood, TX (US)

(73) Assignee: Magnafix, LLC, Kingwood, TX (US)

( * ) Notice: Subject to any disclaimer, the term of this patent is extended or adjusted under 35 U.S.C. 154(b) by 8 days.

(21) Appl. No.: 12/628,990

(22) Filed: Dec. 1, 2009

(65) Prior Publication Data
US 2011/0130617 A1    Jun. 2, 2011

(51) Int. Cl.
*A61N 1/00* (2006.01)

(52) U.S. Cl. ......................................................... 600/14

(58) Field of Classification Search ................ 600/9–15, 600/301; 607/59
See application file for complete search history.

(56) References Cited

U.S. PATENT DOCUMENTS

| | | | |
|---|---|---|---|
| 4,672,951 A * | 6/1987 | Welch | 600/14 |
| 5,034,875 A | 7/1991 | Hattori | |
| 6,524,233 B2 | 2/2003 | Markoll | |
| 6,547,713 B1 * | 4/2003 | Talpo | 600/9 |
| 6,839,595 B2 | 1/2005 | Tepper et al. | |
| 7,175,587 B2 | 2/2007 | Gordon et al. | |
| 7,541,813 B2 | 6/2009 | Synder, Jr. et al. | |
| 2005/0182287 A1 | 8/2005 | Becker | |
| 2009/0216068 A1 | 8/2009 | Thomas et al. | |
| 2010/0010288 A1 * | 1/2010 | Von Ohlsen et al. | 600/9 |

OTHER PUBLICATIONS

Kuz'Min et al. Magnetic therapy apparatus with adaptable electro-magnetic spectrum for treatment of prostatitis and gynecopathies. Biomedical Engineering, vol. 42, No. 2, 2008, pp. 44-46. URL: http://www.spingerlink.com/contect/q030666176660h77.

D'Ovidio et al. Design and experiment of "U" shaped iron-magnetic guideway interacting with HTS "runner" for lift and guidance of vehcile. The 19th International Conference on Magnetically Levitated Systems and Linear Drives. 2006. p. 4; URL: http://www.maglev2006.com/001_D%27Ovidio_ok/001_D%27Ovidio_ok.pdf.

* cited by examiner

*Primary Examiner* — Charles A Marmor, II
*Assistant Examiner* — Christine Hopkins
(74) *Attorney, Agent, or Firm* — Buskop Law Group, PC; Wendy Buskop (57) ABSTRACT

A system, kit, and pet bed for treating tissue using magnetic coils connected to a pulse generator. The system can include a power supply, a bi-directional communication and power port, a microcontroller, a processor, a data storage, and a Helmholtz-like magnetic coil pair. The kit can include a saddlebag and a support strap. The pet bed can include bedding, a fabric housing, a Halbach array, and an on/off switch.

25 Claims, 8 Drawing Sheets

MAGNETIC SYSTEM FOR TREATMENT OF CELLULAR DYSFUNCTION OF A TISSUE OR AN EXTRACELLULAR MATRIX DISRUPTION OF A TISSUE

FIELD

The present embodiments generally relate to a system for therapeutically treating afflicted tissue with magnetic fields that can be worn by a human or an animal such as a dog, a cat, a horse, or another animal.

BACKGROUND

A need exists for an inexpensive portable system for therapeutically treating tissue disease of humans and animals that is non-invasive, easy to apply, and quick to provide relief.

The present embodiments meet these needs.

BRIEF DESCRIPTION OF THE DRAWINGS

The detailed description will be better understood in conjunction with the accompanying drawings as follows.

The present embodiments are detailed below with reference to the listed Figures.

DETAILED DESCRIPTION OF THE EMBODIMENTS

Before explaining the present system in detail, it is to be understood that the system is not limited to the particular embodiments and that the invention can be practiced or carried out in various ways.

The present embodiments relate to a therapeutic system, a pet bed, and a kit for use for treating various ailments. In particular, embodiments can treat injury to the musculoskeletal system, osteoarthritis, and other conditions that result in pain, including pain of the joints, bones, and tissues of the musculoskeletal system.

Various terms are used herein with particular meanings.

The term "pulse blast", as used herein, refers to pulse blasts that can have from about 1 pulse to about 100 pulses contained within the pulse blast. Pulse blasts can be formed using pulses that are not sine-waves, but are square-waves of electrical power delivered to magnetic coils, resulting in an induced magnetic pulse that penetrates tissue that is disposed between or near the magnetic coils.

The term "pulse", as used herein, refers individual pulses that are created and contained within each pulse blast. Multiple pulses can be used to form a pulse blast.

The term "power supply", as used herein, refers to the use of batteries, line power from a wall outlet transformed into DC power at a suitable voltage, or other suitable sources of electrical energy.

The term "bi-directional communication and power port" refers to connectors such as a D-subminiature 9-pin connector.

The term "communication signal" refers to signals used to drive a voltage multiplier, to energize at least two magnetic coils, or to provide a signal to reprogram a microcontroller.

The term "microcontroller" refers to any suitable low voltage microcontroller that is commercially available.

The term "low voltage" refers to a voltage from about 1 volt to about 25 volts.

The term "processor" refers to a component within a microcontroller that makes computations and decisions and is capable of determining precise values of time and logic states for driving elements of the pulse generator, and is capable of comparing a first set of signals to predetermined values stored in an associated data storage in communication with the processor.

The term "data storage" refers to a flash memory, a removable jump drive, a hard drive, or a portion of the microcontroller that is either within or outside of the microcontroller that allows software, firmware, and data to be stored, recalled, modified, and executed therefrom.

The term "computer instructions with preset pulse parameters" refers to computer instructions that define an exact nature of the pulse blasts to be delivered from a pulse generator.

As the term is used herein, "vectors" refers to a mathematical representation of a magnetic field which contains quantitative information about both the magnetic field direction and the field amplitude or strength.

The term "normal-to plane axis", as used herein, refers to an axis that is perpendicular to a plane surface of an individual coil or a coil array encapsulated within a flexible polymer. For example, if the magnetic coil is elliptical, the plane surface would be the plane of the first surface of the elliptical shaped magnetic coil.

The term "mechanically flexible polymer coating", as used herein, refers to a flexible, bendable, not brittle coating that can contain an elastomeric material such as silicone or a urethane. In embodiments, the mechanically flexible polymer coating can be a washable, heat resistant thin coating of a polymer such as a polypropylene homopolymer, a polypropylene copolymer, or a cross linked polymer of polypropylene and polyethylene, forming a bendable, impact resistant, coating such as coatings used to encapsulate electrical wires. The mechanical flexible polymer coating can be a laminate with a first coating covering a second coating that encapsulates the magnetic coils while allowing the magnetic coils to be flexed and bent into a desired shape.

The term "computer instructions in the data storage for instructing the processor to generate random pulse blasts, random pulses, or randomization of selected pulse parameters according to a random pulse generator, as the dosage amounts within the specified range of pulse parameters" refers to a series of algorithmic computer codes that can allow the pulse generator to sequentially generate pulses or pulse blasts with a predetermined number of pulses in the pulse blasts and having a predetermined time interval between the pulse blasts or pulses. In embodiments, a random number generator can be used to generate variable pulse blasts in the dosage amounts.

The phrase "saddlebag" refers to a single pouch or a configuration of two pouches connected together which can reside on a back of an animal. The saddle bag can have a first pouch riding on a first side of an animal connected to a second pouch riding on a second side of the animal, so as to allow for safe carriage of the power supply and the pulse generator by an animal. A support strap can wrap around the front or chest area of the animal enabling the two pouches to stay securely on the animal for therapeutic purposes.

As this term is used herein, the "magnetic Halbach array" can be an array of magnetic elements in a 1-dimensional (linear) or a 2-dimensional (planar) array wherein in-plane magnetic field generators reside in the magnetic Halbach array and can act to produce large amplitude magnetic fields on one side of the magnetic Halbach array, while producing a minimal magnetic field on the other side of the magnetic Halbach array.

The term "animal actuated on/off switch" refers to a simple mechanical pressure switch, an optical detector switch, a heat detector switch, a motion detector switch, a capacitance proximity detector switch, a sound or vibration detector switch, an ultrasonic detector switch, or similar means by which the presence of an animal can be established and detected by the microcontroller.

The term "heating element" refers to an electrical element that allows the generation of controlled heat which can be applied to pet bedding.

The term "cooling element" refers to an electrical element such as an array of Peltier devices, which allow heat to be removed from part or all of a pet bed or other animal bedding.

The magnetic coil can be an electro-magnetic coil.

Embodiments can be used for treatment of a cellular dysfunction of tissue or an extracellular matrix disruption of a tissue, or both of these problems, and can use a pulse generator and at least one pair of magnetic coils.

Embodiments can also be used to accelerate healing of bone, skin, nerves, musculoskeletal systems, and cardiovascular systems.

Embodiments can be used to promote the healing of refractory or non-healing bone fractures; to reduce swelling from osteoarthritis or rheumatoid arthritis; to reduce scar tissue formation in skin, tendons, muscles and ligaments; to reduce infection rate; and to promote increased joint range of motion subsequent to injury or a degenerative disease.

Embodiments can be used to treat or reduce pain including: idiopathic joint pain, pain associated with fibromyalgia, lower back pain, compartment pain, referred pain, acute pain, chronic pain, and migraines.

Embodiments can be used to treat strains of muscles, tendons, ligaments, bulging vertebral disks, osteopenia, temporomandibular joint, and craniofacial structures.

Embodiments can be used to treat: critical defects in bone; injured cardiovascular tissues; heart failure; heart injury by reducing monocyte-induced swelling; spinal cord injury by promoting nerve re-growth, inhibiting fibroblast infiltration and growth, and inhibiting scar formation; nerve injury; nerve degeneration; loss of bladder or bowel control; neurogenic incontinence; neurogenic erectile dysfunction; ulcers; injury to the rotator cuff; internal organ disorders including liver, pancreas, kidney and lung disease; tremors associated with Parkinson's disease, ataxia, or multiple sclerosis; non-responsive wounds including diabetic foot ulcer and post-surgical abdominal ulcer; and to treat cancer by inhibiting tumor formation and growth.

Embodiments can be used to improve: outcome and to accelerate healing after surgery or injury of the cornea including LASIK surgery and corneal transplants; engraftment of surgical implants; ejection fraction after surgery for heart failure; cardiac muscle regeneration; functional outcome after heart surgery as measured by the 6-minute walk test; blood flow in ischemic limbs; limb salvage after removal of blood flow; or strength of tissues following injury.

Embodiments can also be used to: decrease cardiac scarring after heart failure or surgery; accelerate nerve regeneration; treat strokes by improving blood flow to the affected areas of the brain; reduce functional loss following a stroke; and recover tone of the muscles of the urogenital system.

Embodiments can be used as an adjunct to stem cell therapy: to improve engraftment; for in vivo amplification of stem cells, to accelerate phenotypic development of the stem cells into the desired tissue phenotypes, for targeting engraftment, and for guiding phenotypic development into the desired tissue types.

The pulse generator can provide a signal to or excite at least one Helmholtz-like magnetic coil pair in communication with the pulse generator. The Helmholtz-like magnetic coil pair can generate a plurality of pulse blasts when the pulse generator sends the signal or excites the Helmholtz-like magnetic coil pair. Each pulse blast can be formed from one or more pulses. The pulse generator can have at least one power supply such as two connected batteries or a battery and a battery charger. An electrical current can be generated by the power supply or the pulse generator.

The pulse generator can have a bi-directional communication and power port for flowing power into and out of the pulse generator and flowing communication signals into and out of the pulse generator.

The pulse generator can have a microcontroller in communication with the bi-directional communication and power port.

The microcontroller can have a processor that can be in communication with the power supply. Data storage can be in communication with the processor and computer instructions with preset pulse parameters can be stored in the data storage.

A pair of first transistors can be in communication with the microcontroller. In embodiments, multiple pairs of first transistors can be in communication with the microcontroller.

The first pair of transistors can allow the microcontroller to control power flow into the voltage multiplier.

A voltage multiplier can be connected to the at least one pair of first transistors. The voltage multiplier can include one or more diodes and one or more capacitors. The voltage multiplier can include combinations of diodes and capacitors for communication with the microcontroller for increasing or decreasing the output voltage of the pulse generator.

In embodiments, the diodes can be rapid switching diodes, and the capacitors can be surface mount ceramic capacitors.

In embodiments, the voltage multiplier can be a Villard Cascade Voltage Multiplier, though other configurations may be employed.

The pulse generator can have a pair of second transistors in communication with the voltage multiplier to form an output stage. In embodiments, the pulse generator can have multiple second transistors. The second transistors can be controlled by the microcontroller to form or produce an electrical signal to send to a Helmholtz-like magnetic coil pair to generate a plurality of pulse blasts or pulses.

In embodiments, the second transistors can allow a microcontroller to control electrical energy flow from the pulse generator to magnetic coils; thereby controlling pulse parameters.

Embodiments can further include a pair of power supply conduits, which can be wires that each connect to at least one pair of magnetic coils. The pair of power supply conduits, such as those connecting the power supply to the pulse generator, or connecting the pulse generator to the coils, can be wires.

Embodiments can include at least one Helmholtz-like magnetic coil pair sized to generate a plurality of pulse blasts which can have a slew rate of at least 200 kiloGauss per second (kG/s).

Each Helmholtz-like magnetic coil pair can have a first magnetic coil with a first magnetic coil diameter and a first magnetic coil axis. A first magnetic coil first side can have a first polarity, and a first magnetic coil second side can have a second polarity. The first magnetic coil can connect to one of the pair of power supply conduits.

The Helmholtz-like magnetic coil pair can have a second magnetic coil with a second magnetic coil diameter and a second magnetic coil axis. A second magnetic coil first side can have a first polarity, and a second magnetic coil second side can have a second polarity. The second magnetic coil can connect to one of the power supply conduits.

The first magnetic coil can be disposed opposite the second magnetic coil, enabling the formed Helmholtz-like magnetic coil pair to treat tissue placed between or proximate the first and second magnetic coils.

In each Helmholtz-like magnetic coil pair, the first magnetic coil and second magnetic coil can be disposed at separations from about 0.1 radius to about 20 radii.

The first magnetic coil and second magnetic coil can be oriented so that when energized using the pulse generator, a plurality of magnetic square-wave pulses can be generated with slew rates of at least 200 kG/s for at least a duration about 0.1 microsecond to about 200 microseconds without forming a sine shaped pulse wave.

Each formed magnetic square-wave pulse can have a leading edge and a trailing edge. Each leading edge to trailing edge can have a duration of about 0.1 microsecond to about 200 microseconds. Each leading or trailing edge can maintain a slew rate of at least about 200 kG/s.

In embodiments, pulse parameters controlled by the microcontroller can include: a pulse voltage, a pulse duration, a pulse polarity, a number of pulses per unit of time; a number of pulses per pulse blast, a time duration between pulses in each pulse blast, a time duration between pulse blasts, or combinations thereof.

In one or more embodiments, the pulse voltage can range from about 5 volts to about 200 volts.

In embodiments, the pulses can be bipolar pulses.

In embodiments, an external power supply, such as a 110 volt wall outlet or a generator, can be connected to the power supply to allow for uninterrupted pulse blast generation for a dosage amount of time. The external power supply can also be a single battery or a plurality of connected batteries. The pulse generator can have an on/off switch for actuating the external power supply to supply power to the pulse generator.

The external power supply can be one or more DC batteries, such as 4 "C" batteries, 2 or more "AA" batteries, or one or more 9 volt batteries. The pulse generator can be run on 110 volts of power provided that there is a current conditioning device secured to the generator. In one or more embodiments, the pulse generator can run on 220 volts AC. For example, the pulse generator can be configured to be operated using common United Stated line voltage or common European line voltage.

In embodiments, between about 2 transistors to about 40 transistors can be utilized. The capacitor and the first and second transistor pairs can be connected together in an H-bridge configuration.

The microcontroller can include computer instructions, such as a soft remote terminal unit instruction, allowing the microcontroller to be reconfigurable on-line, without any down time of the pulse generator. The pulse generators of an array of pulse generators can be reconfigured on-line using communication from an administrative server in communication with the pulse generators through a network which can be a wireless network.

Each pulse blasts can be a positive polar blast, a negative polar blast, or combinations thereof. The pulse blasts can include different numerical quantities of pulses. Differing intervals of time can occur between pulse blasts The alignment of the axis of each magnetic coil can range from being parallel and coaxial to being anti-parallel, adjacent, and coplanar. A plurality of the pairs of magnetic coils can be formed into a magnetic array with a common controller for treating a large area of tissue. The magnetic array can be formed to surround an entire limb.

The magnetic array can generate pulses in controlled sequences to produce a plurality of magnetic field vectors that rotate through a space proximate to the magnetic array over a preset unit of time and/or that translate through the space near the magnetic array over time.

The magnetic array can be a set of magnetic coils arranged in such a manner as to allow one common controller to energize or de-energize any combination of magnetic coils in the magnetic array; thereby allowing the common controller to control the resulting magnetic field within and near the magnetic array.

The common controller of the magnetic array can be a microcontroller which controls the pulse generator to generate pulses or pulse blasts which can be communicated to a pair of magnetic coils or a magnetic coil array.

The plurality of magnetic coils can be arranged into a member of the group consisting of: a two dimensional Halbach array, a one dimensional Halbach array, and combinations thereof.

At least one pair of magnetic coils of each Halbach arrays can have an in-plane axis to act as a flux conduit between a normal-to-plane axis of at least one other pair of magnetic coils.

Each Halbach array can contain flux concentrators of iron, ferrite or similar magnetic material to concentrate the magnetic field at specified points within each Halbach array.

The distance between the pairs of magnetic coils in each Halbach array can be adjusted to range from about 0.5 inches to about 10 inches, measured as the center-to-center distance between the normal-to-plane axis.

Each Halbach array can be sealed within a mechanically flexible polymer coating, which allows for the generation of magnetic fields to be unimpeded. Each Halbach array can be mechanically flexible and conformable to adapt to a curvature of an anatomic surface of a head, a neck, a torso, a pelvis, a limb, or combinations thereof.

In embodiments, additional computer instructions can be in the data storage of the pulse generator for instructing the processor to generate, at random intervals, pulse blasts or pulses as the dosage amounts within the specified range of pulse parameters. Pulses with a duration longer than about 200 microseconds can be used to produce unipolar magnetic pulses.

The pair of magnetic coils can be coils readily formed from multiple turns of suitable electrical wire or another form of electrical conductor. The magnetic coil diameters can be measured as the average diameter across any of the magnetic coils in the system. Each magnetic coil can have an axis that is perpendicular to the plane in which the magnetic coils are wound, and through the center of each magnetic coil.

In embodiments, the Helmholtz-like magnetic coil pair can be defined to be a configuration of two electrical coils that are magnetically aligned north-to-south on the same axis and separated by some distance. The distance of separation can be adjusted to accommodate the shape, thickness, and physical disposition of the tissue to be treated and the surrounding tissues and anatomical structures, but only when the distance between the coils is not limited to the strict definition of a Helmholtz coil pair.

The plurality of magnetic square-wave pulses can be generated as a result of the electrical energy discharged through each of the magnetic coils as the pulses are originated from the pulse generator.

Embodiments can include a kit for therapeutically treating animal tissue ailments including cellular dysfunction of a tissue or an extracellular matrix disruption of a tissue.

The kit can include an animal saddlebag with a first pouch and a second pouch connected by a support strap for holding the first pouch and second pouch together across a chest of an animal. The animal can be a four legged animal, such as a dog, a horse, a deer, or another animal.

A pulse generator can be placed or disposed in one of the pouches. At least one pair of magnetic coils can be placed or disposed in another pouch of the saddlebag, enabling the placement of damaged tissue between the magnetic coils.

The saddlebag can be used to place the magnetic coils adjacent to a site of cellular dysfunction or adjacent to a site of tissue having an extracellular matrix disruption.

Each pair of magnetic coils can be connected to the pulse generator through a power supply conduit.

Embodiments of the kit can include a pet bed for therapeutically treating an animal. The pet bed can include bedding contained in a fabric housing. A Halbach array of magnetic coils can be disposed in the fabric housing.

An animal actuated on/off switch can be connected to the Halbach array and to the pulse generator.

Magnetic pulse blasts can be generated when an animal actuates the animal actuated on/off switch.

Additionally, the pet bed can contain a heating element connected to a power source of the Halbach array disposed within the fabric housing. The heating element can be controlled by a microcontroller in the fabric housing that can be actuated when the animal engages the animal actuated on/off switch.

The animal actuated on/off switch can be a pressure sensitive switch, a movement sensitive switch, or a heat sensitive switch.

The pet bed can include a cooling element connected to the power source of the Halbach array. The cooling element can be disposed within the fabric housing. The cooling element can be controlled by the microcontroller providing cooling when the animal engages the animal actuated on/off switch.

The pet bed can include pet bedding. Pet bedding can include any of a variety of arrangement of structures which an animal will rest or sleep. For example, a dog bed can have cedar chips as the pet bedding. A horse can have straw as the pet bedding. A cat can have strips of fabric as the pet bedding. The pet bedding can be contained within the fabric housing, such as a corduroy material or canvas, enabling an animal to rest or to sleep.

The magnetic coils, the heating and/or cooling elements, and detector switches can be placed within the fabric housing.

Figure 1:
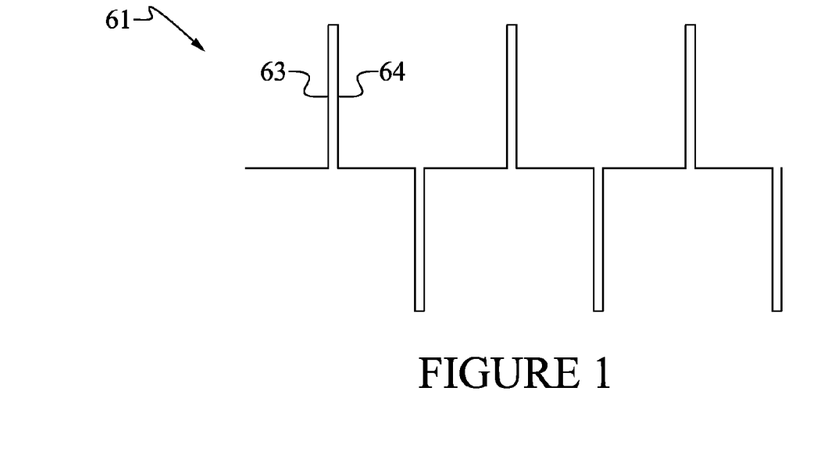
FIG. 1 is a diagram a square-wave produced with a pulse generator.

Turning now to the Figures, FIG. 1 shows an example of a typical square-wave 61 usable in a pulse blast with a leading edge 63 and a trailing edge 64. Each leading edge to trailing edge can have a duration of between about 0.1 microsecond to about 200 microseconds and can maintain a slew rate of at least 200 kG/s.

Figure 2:
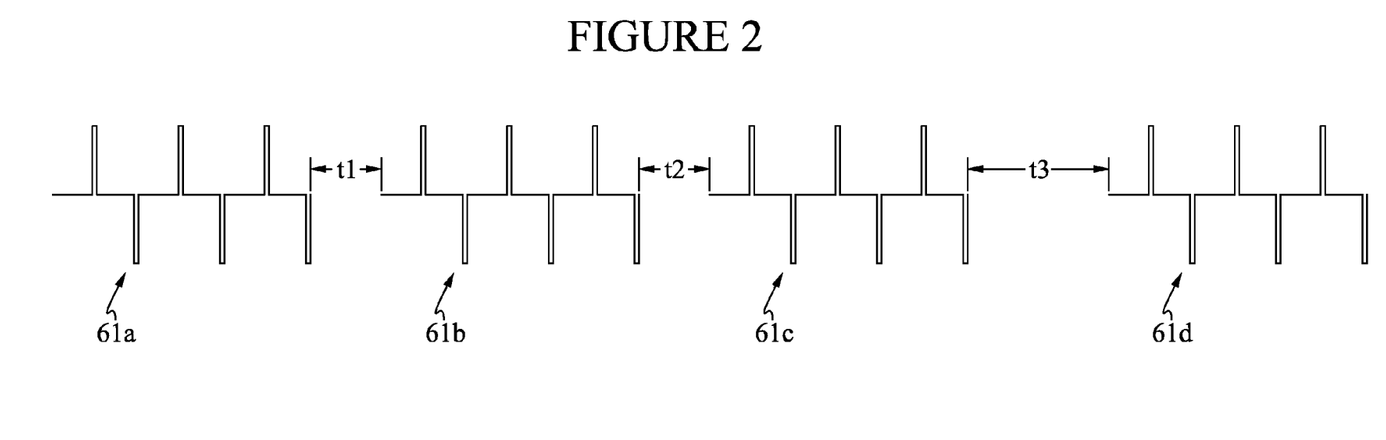
FIG. 2 is a diagram showing four square-waves as a pulse blast.

FIG. 2 shows four square-waves 61a, 61b, 61c, and 61d forming a pulse blast. The first square-wave 61a is shown with a time duration of t1 away from the second square-wave 61b. The third square-wave 61c is shown with a time duration t2 equivalent to the time duration between the first and second square-waves. The fourth square-wave 61d is shown with a time t3 duration from the third square-wave which can be double the time durations between the first and second square-waves.

Figure 3:
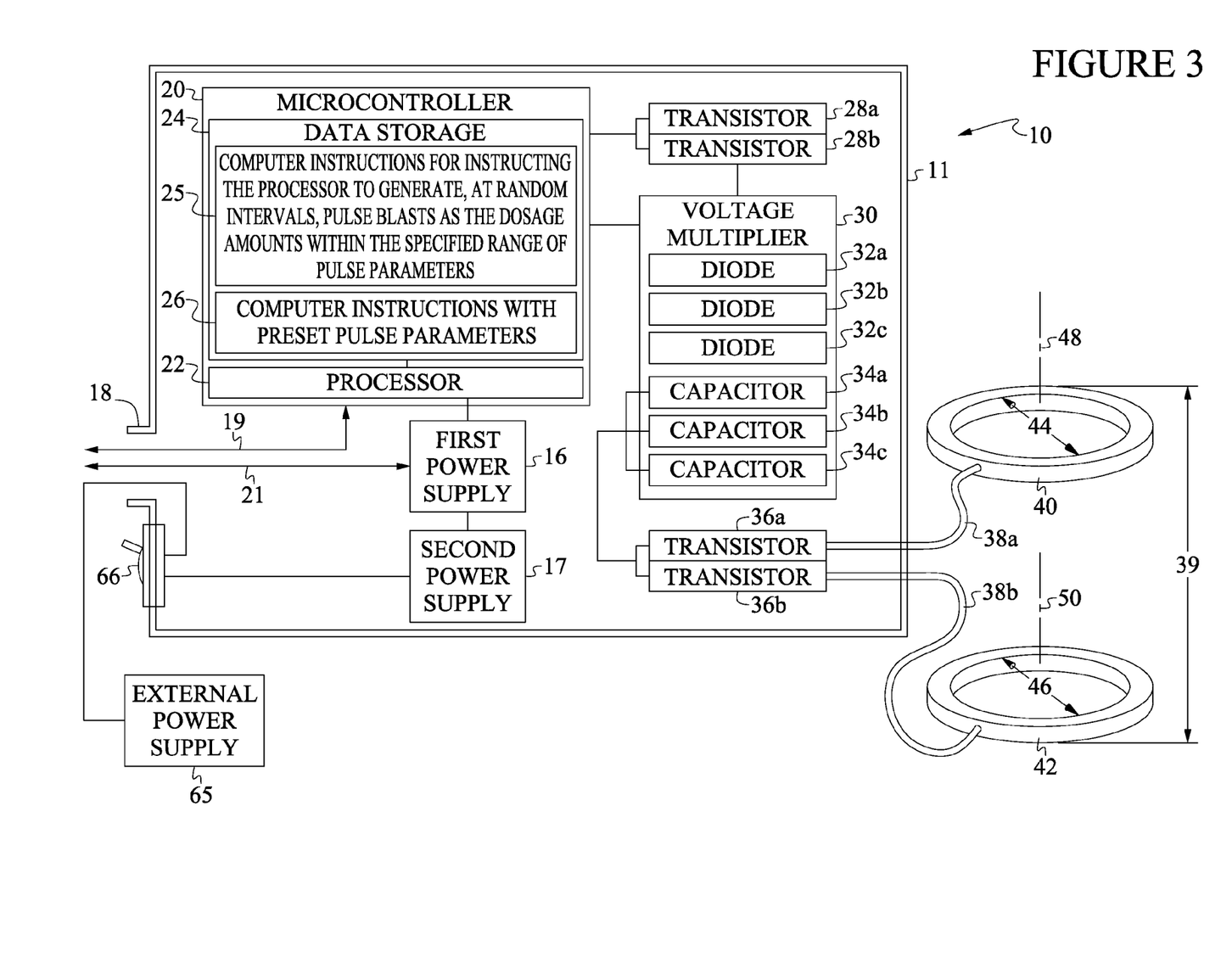
FIG. 3 is a diagram of the pulse generator.

FIG. 3 depicts a pulse generator 10 usable in the invention. The pulse generator 10 has a housing 11. In the housing 11 are electronics that generate a plurality of pulse blasts. The pulse generator 10 has a first power supply 16 and a second power supply 17.

A bi-directional communication and power port 18 flows power 21 into and out of the pulse generator 10, and flows communication signals 19 into and out of the pulse generator 10. The bi-directional communication and power port 18 can be formed in the housing 11 of the pulse generator 10.

A microcontroller 20 is shown in communication with the bi-directional communication and power port 18. The microcontroller 20 has a processor 22 in communication with either the first power supply 16 or the second power supply 17. The microcontroller 20 also has a data storage 24 in communication with the processor 22. In the data storage 24 are computer instructions 26 with preset pulse parameters.

Also shown are computer instructions 25 in the data storage for instructing the processor to generate at random intervals, pulse blasts, pulses as the dosage amounts within the specified range of pulse parameters.

A first pair of transistors 28a and 28b is in communication with the microcontroller 20.

A voltage multiplier 30 is connected to the first pair of transistors 28a and 28b. The voltage multiplier 30 has three diodes 32a, 32b, and 32c, as well as three capacitors 34a, 34b, and 34c. The voltage multiplier 30 is in communication with the microcontroller 20 for increasing or decreasing the voltage of electricity of the pulse generator 10.

A second pair of transistors 36a and 36b are shown connected to the three capacitors 34a, 34b, and 34c. The second pair of transistors 36a and 36b form at least one of a plurality of pulses and/or a pulse blast that are emitted by the pulse generator 10.

A pair of power supply conduits 38a and 38b are shown connected to the second pair of transistors 36a and 36b.

A Helmholtz-like magnetic coil pair 39 is connected to the pair of power supply conduits 38a and 38b. The Helmholtz-like magnetic coil pair 39 is sized to generate a plurality of pulse blasts with a slew rate of at least 200 Kilogauss per second (kG/s).

The Helmholtz-like magnetic coil pair 39 is shown with a first magnetic coil 40 with a first magnetic coil diameter 44 and a first magnetic coil axis 48. A second magnetic coil 42 is also shown, with a second magnetic coil diameter 46 and a second magnetic coil axis 50.

FIG. 3 also shows an external power supply 65 connected to the second power supply 17 through an on/off switch 66 to allow for uninterrupted pulse blast generation for a dosage amount of time. The on/off switch 66 allows for actuation of the external power supply 65 to supply power to at least the first power supply 16 or second power supply 17.

Figure 4:
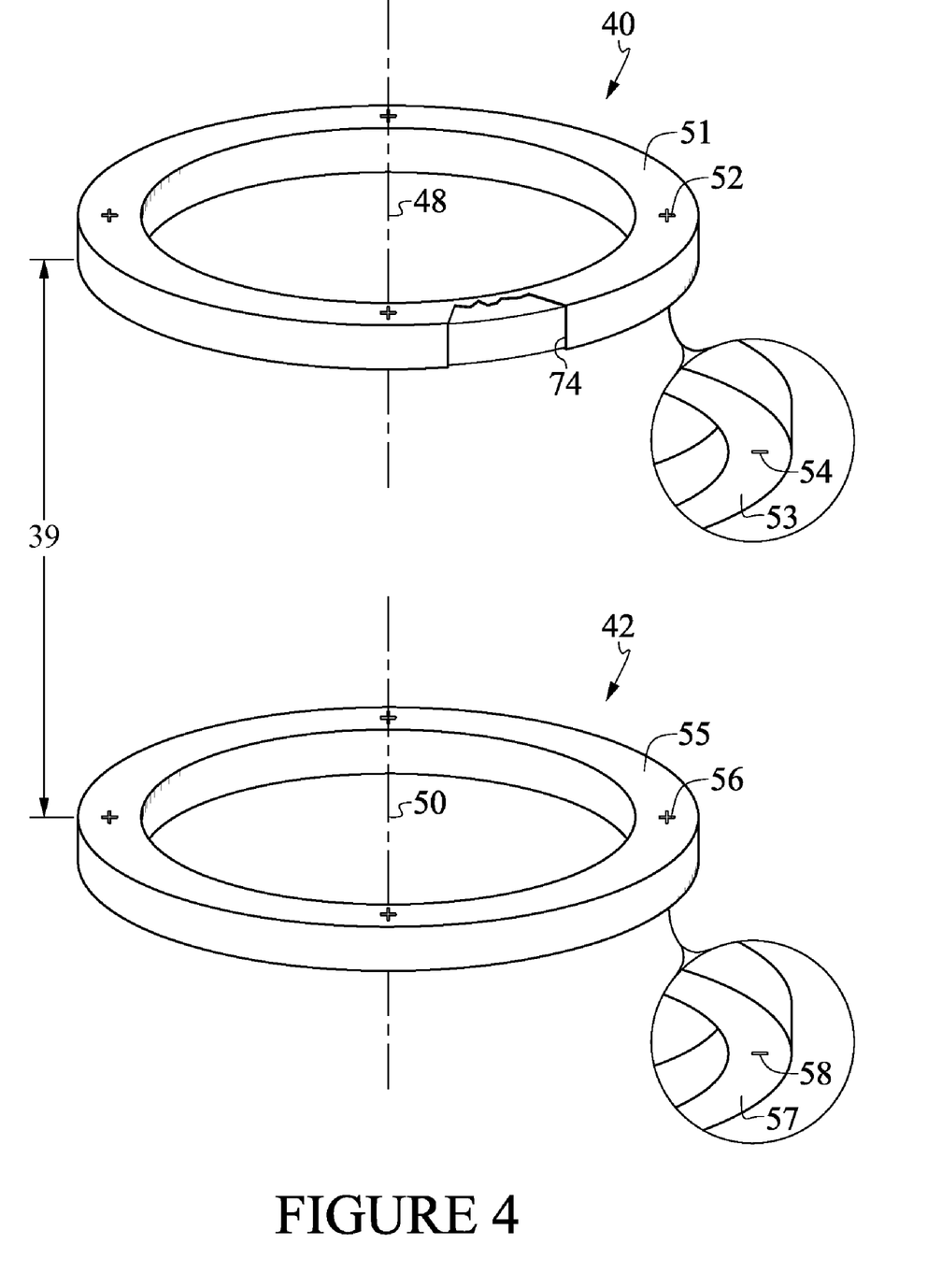
FIG. 4 is a detailed view of two of the magnetic coils usable in the system.

FIG. 4 shows a detailed view of the Helmholtz-like magnetic coil pair 39. The first magnetic coil 40 with the first magnetic coil axis 48 is shown.

First magnetic coil first side 51 with first polarity 52 and first magnetic coil second side 53 with second polarity 54 are shown.

Also shown is second magnetic coil 42 with the second magnetic coil axis 50. Second magnetic coil first side 55 is shown with first polarity 56, and second magnetic coil second side 57 is shown with second polarity 58.

FIG. 4 shows that each of the magnetic coils can be encapsulated with a mechanically flexible polymer coating 74 which allows unimpeded the generation of the magnetic fields.

Figure 5:
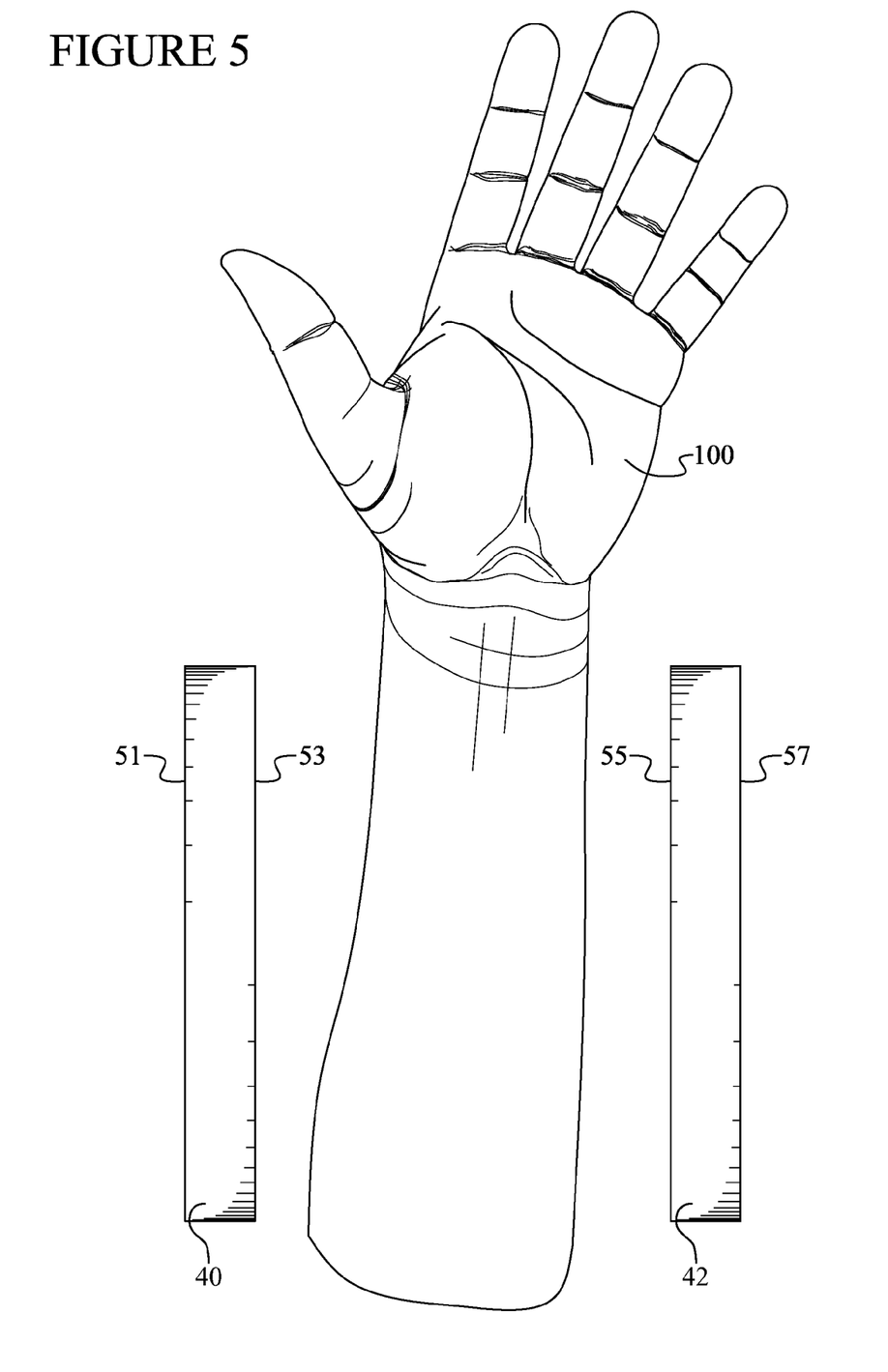
FIG. 5 is a detailed view of an arrangement of magnetic coils around a limb.

FIG. 5 shows the orientation of the Helmholtz-like magnetic coil pair for therapeutic treatment. The first magnetic coil first side 51 is disposed opposite the second magnetic coil second side 57 for treatment of cellular dysfunction of a tissue 100 placed between the first magnetic coil 40 and second magnetic coil 42; for treatment of an extracellular matrix disruption of a tissue placed between the first and second magnetic coils; or combinations of these therapeutic treatments.

The first magnetic coil 40 and second magnetic coil 42 can be oriented so that when they are energized using the pulse generator 10, a plurality of magnetic square-wave pulses can be generated with slew rates of at least 200 kG/s for at least a duration between about 0.1 microsecond to about 200 microseconds without forming a sine shaped pulse wave.

Also shown are first magnetic coil second side 53 and second magnetic coil first side 55.

Figure 6:
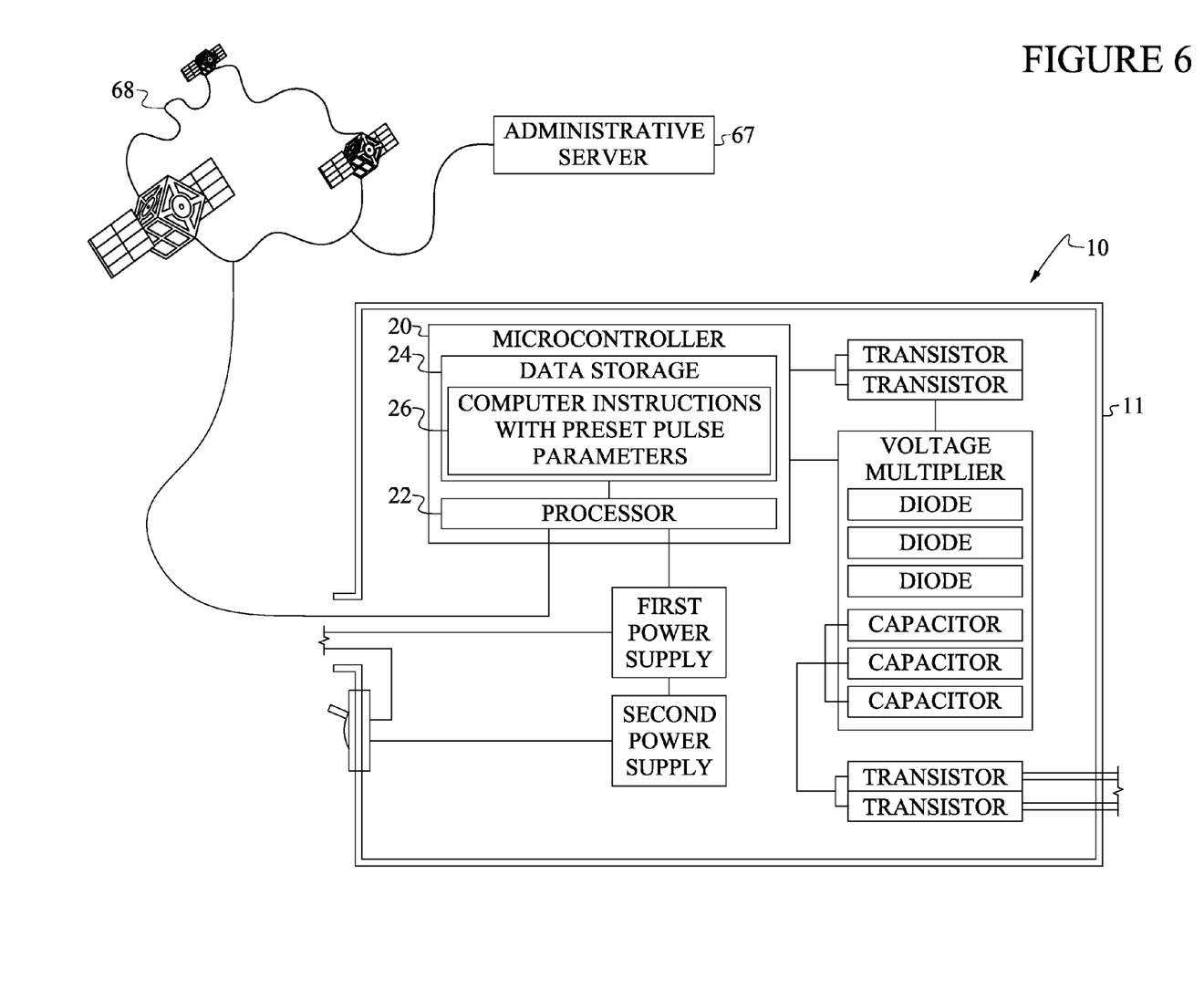
FIG. 6 is a diagram showing a processor in communication with an administrative server.

FIG. 6 shows an embodiment of the pulse generator 10 with the microcontroller 20 having a processor 22 in communication with at least one network 68 with an administrative server 67, that allows for online reconfiguration of the pulse generator.

Also shown are the housing 11, the data storage 24, and the computer instructions 26 with preset pulse parameters.

Figure 7:
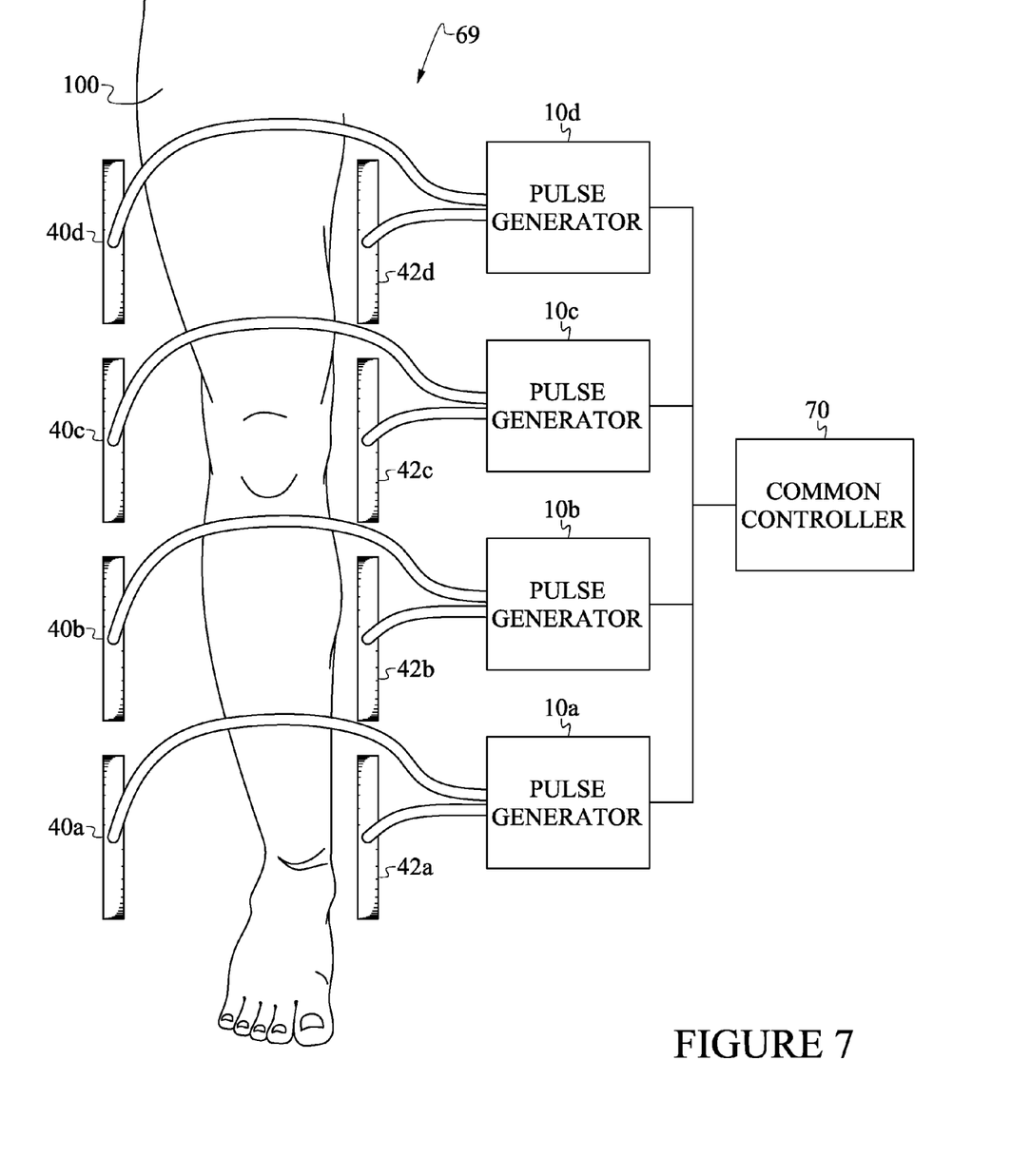
FIG. 7 is diagram of a magnetic array applied over a limb.

FIG. 7 shows four Helmholtz-like magnetic coil pairs having first magnetic coils 40a, 40b, 40c, and 40d paired with second magnetic coils 42a, 42b, 42c, and 42d.

Each magnetic coil pair is associated with a pulse generator 10a, 10b, 10c, and 10d. The pulse generators are controlled by a common controller 70.

The multiple pairs of magnetic coils with pulse generators form a magnetic array 69 for treating a large area of tissue 100 that is capable of covering an entire limb, which is a leg in this view.

Figure 8A:
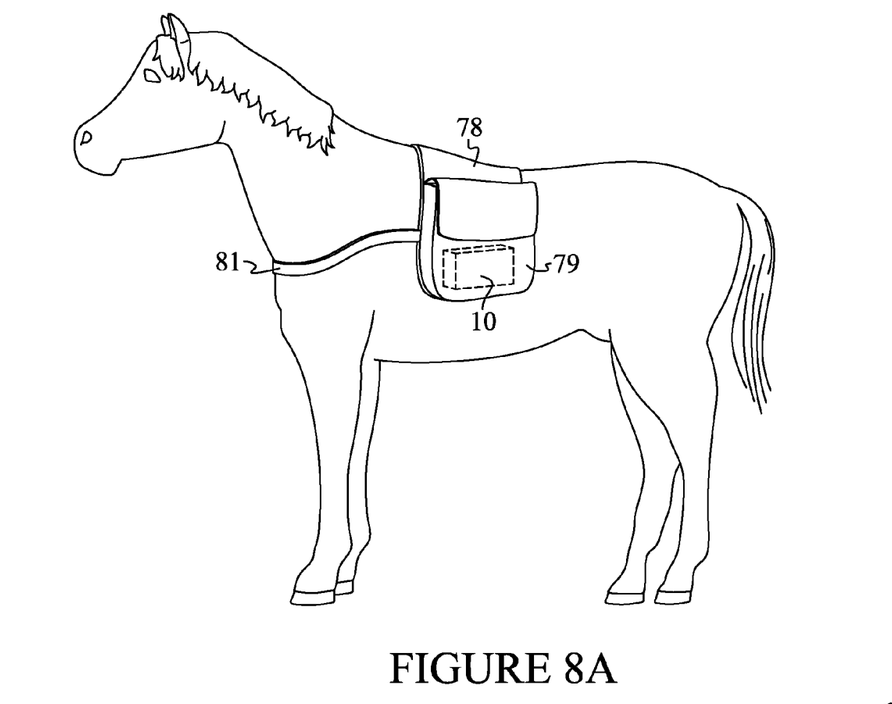
FIG. 8A is an animal wearing a kit of the invention.

FIG. 8A shows an embodiment of a kit for therapeutically treating tissue ailments including cellular dysfunction of a tissue or an extracellular matrix disruption of a tissue, with an animal saddlebag 78, a first pouch 79, a pulse generator 10 in the first pouch 79, and a support strap 81.

Figure 8B:
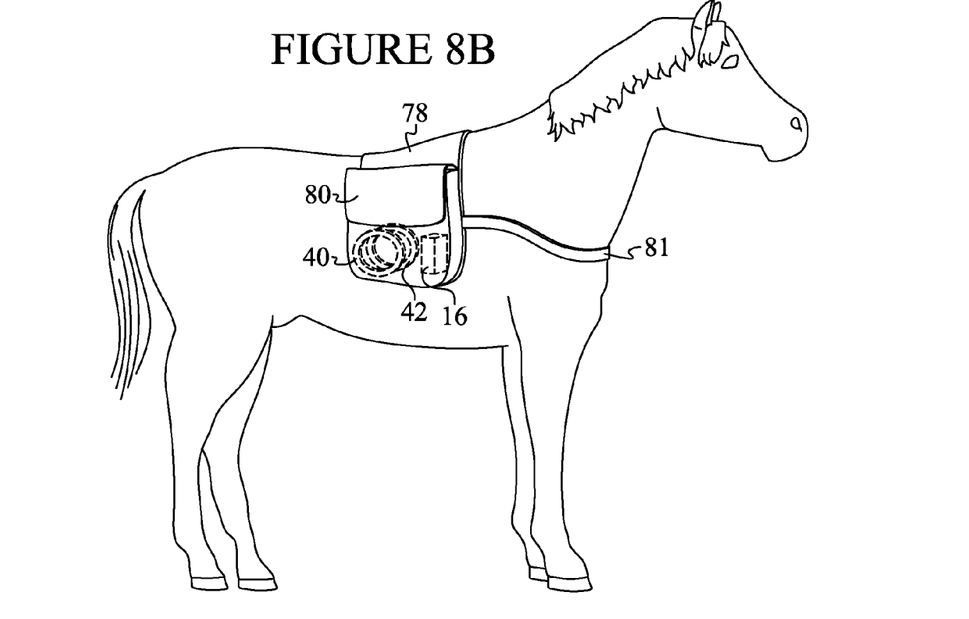
FIG. 8B shows the opposite side of the animal shown in FIG. 8A.

FIG. 8B shows the opposite side of the animal shown in FIG. 8A. The animal saddlebag 78 is shown with a second pouch 80.

Within the second pouch 80 is a first magnetic coil 40, second magnetic coil 42 and first power supply 16.

The support strap 81 holds the first pouch 79 and second pouch 80 together across the chest of the animal.

Figure 9:
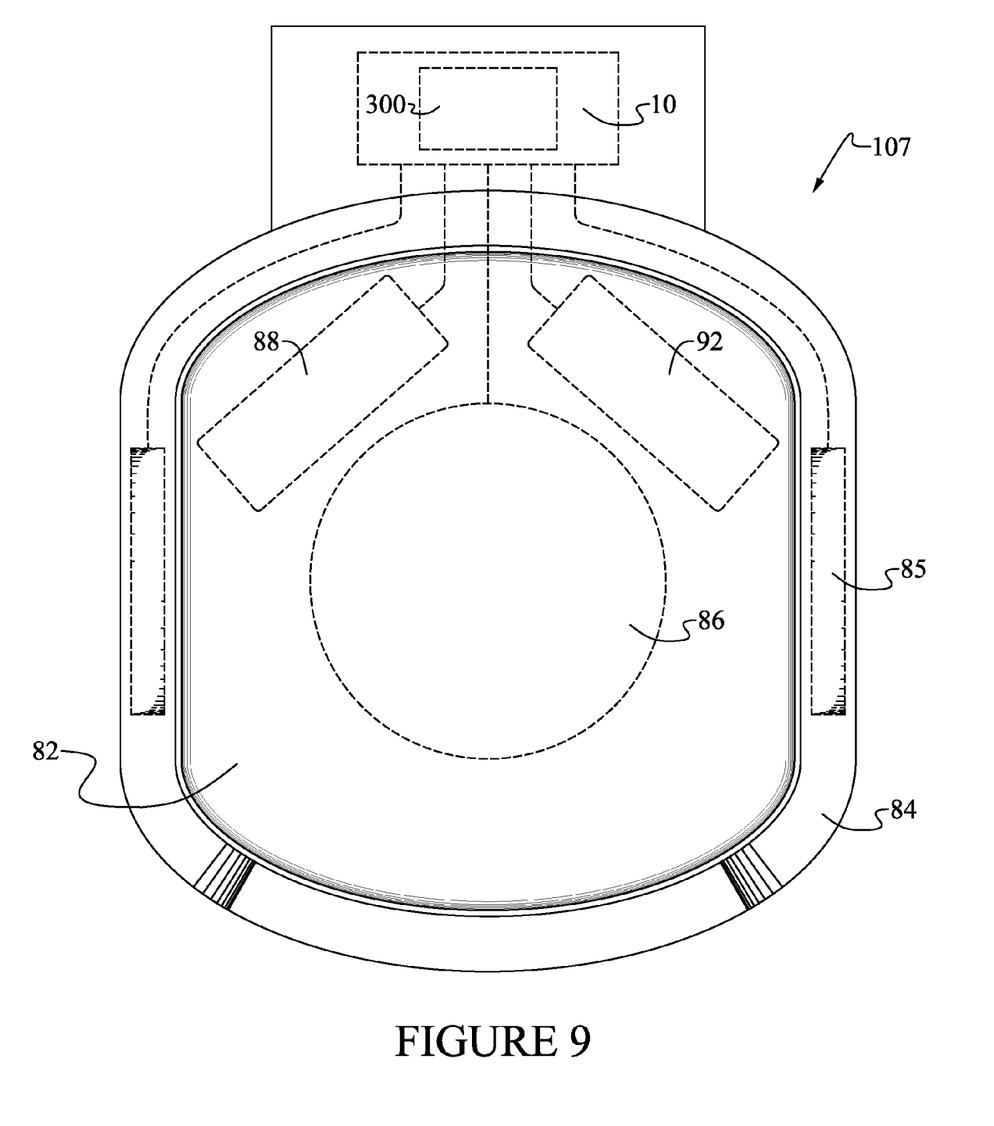
FIG. 9 is a view of a pet bed of the invention.

FIG. 9 shows and embodiment of a pet bed 107 of the invention.

The pet bed has bedding 82, a fabric housing 84 for containing the bedding 82, a Halbach array 85 disposed in the fabric housing 84, and an animal actuated on/off switch 86 connected to the Halbach array 85.

Also shown are a heating element 88 and a cooling element 92, each connected to a power supply 300 of the pulse generator 10.

While these embodiments have been described with emphasis on the embodiments, it should be understood that within the scope of the appended claims, the embodiments might be practiced other than as specifically described herein.

What is claimed is:

1. A system for treatment of ailments, wherein the system comprises:
   a. a pulse generator comprising:
      i. a power supply connected to an external power supply to allow for uninterrupted pulse blast generation for a dosage amount of time;
      ii. a bi-directional communication and power port for flowing power into and out of the pulse generator and flowing communication signals into and out of the pulse generator;
      iii. a microcontroller in communication with the bi-directional communication and power port, wherein the microcontroller comprises a processor in communication with the power supply;
      iv. a data storage in communication with the processor;
      v. computer instructions with preset pulse parameters in the data storage;
      vi. at least one pair of first transistors in communication with the microcontroller;
      vii. a voltage multiplier in communication with the at least one pair of first transistors, wherein the voltage multiplier comprises a plurality of diodes and a plurality of capacitors in communication with the microcontroller for increasing or decreasing a voltage of the pulse generator;
      viii. at least one pair of second transistors in communication with at least one of the plurality of capacitors, wherein the at least one pair of second transistors produces a signal; and
      ix. a first and second power supply conduit in communication with the at least one pair of second transistors; and
   b. a Helmholtz-like magnetic coil pair in communication with the pulse generator for receiving the produced signal, wherein the Helmholtz-like magnetic coil pair is sized to generate a plurality of pulse blasts when excited by the pulse generator, wherein each pulse blast comprises a plurality of pulses, wherein the plurality of pulse blasts have a slew rate of at least 200 kiloGauss per second, and wherein the Helmholtz-like magnetic coil pair comprises:
      i. a first magnetic coil with a first magnetic coil first side and a first magnetic coil second side, wherein the first magnetic coil first side has a first polarity and the first magnetic coil second side has a second polarity, and wherein the first magnetic coil is in communication with the first power supply conduit; and
      ii. a second magnetic coil with a second magnetic coil first side and a second magnetic coil second side, wherein the second magnetic coil first side has a first polarity and the second magnetic coil second side has a second polarity, wherein the second magnetic coil is in communication with the second power supply conduit, and wherein the first magnetic coil is disposed opposite the second magnetic coil enabling the Helmholtz-like magnetic coil pair to:
      iii. treat cellular dysfunction of a tissue placed between the first and second magnetic coils; and
      iv. treat an extracellular matrix disruption of a tissue placed between the first and second magnetic coils, or combinations thereof, wherein the first magnetic coil and second magnetic coil are oriented so that when the first and second magnetic coils are energized using the pulse generator a plurality of magnetic square-wave pulses are generated for at least a duration from 0.1 microsecond to 200 microseconds without forming a sine shaped pulse wave.

2. The system of claim 1, wherein the preset pulse parameters are controlled by the microcontroller and are selected from the group consisting of: a pulse voltage, a pulse duration, a pulse polarity, a number of pulses per unit of time, a number of pulses per pulse blast, a time duration between pulses in each pulse blast, and a time duration between pulse blasts.

3. The system of claim 2, wherein the pulse voltage ranges from 5 volts to 200 volts.

4. The system of claim 1, wherein the pulses are bipolar.

5. The system of claim 1, wherein the pulse generator further comprises an on/off switch for actuating the external power supply to pass power to the pulse generator.

6. The system of claim 1, wherein the plurality of capacitors and the at least one pair of second transistors are connected together in an H-bridge configuration.

7. The system of claim 1, wherein the microcontroller is adapted for online reconfiguration using communication from an administrative server.

8. The system of claim 7, wherein the administrative server and the microcontroller are in wireless communication through at least one network.

9. The system of claim 1, wherein the plurality of pulse blasts are positive polar blasts, negative polar blasts, or combinations thereof.

10. The system of claim 1, wherein a spacing exists between the first magnetic and second magnetic coil that can range from 0.1 to 20 times a radius of the magnetic coils.

11. The system of claim 1, wherein an alignment of an axis of each magnetic coil exists that can range from being parallel and coaxial to being anti-parallel, adjacent, and coplanar.

12. The system of claim 1, wherein the plurality of pulse blasts comprises different numerical quantities of pulses.

13. The system of claim 1, wherein differing intervals of time occur between each pulse blast.

14. The system of claim 1, further comprising computer instructions in the data storage for instructing the processor to generate, at random intervals, pulse blasts as dosage amounts within specified ranges of pulse parameters.

15. The system of claim 1, wherein each pulse has a duration of longer than 200 microseconds for producing unipolar magnetic pulses with leading edge magnetic slew rates greater than 200 kiloGauss per second and trailing edge magnetic slew rates less than 200 kiloGauss per second.

16. A system for treatment of ailments, wherein the system comprises:
  a. a pulse generator comprising:
    i. a power supply;
    ii. a bi-directional communication and power port for flowing power into and out of the pulse generator and flowing communication signals into and out of the pulse generator;
    iii. a microcontroller in communication with the bi-directional communication and power port, wherein the microcontroller comprises a processor in communication with the power supply;
    iv. a data storage in communication with the processor;
    v. computer instructions with preset pulse parameters in the data storage;
    vi. at least one pair of first transistors in communication with the microcontroller;
    vii. a voltage multiplier in communication with the at least one pair of first transistors, wherein the voltage multiplier comprises a plurality of diodes and a plurality of capacitors in communication with the microcontroller for increasing or decreasing a voltage of the pulse generator;
    viii. at least one pair of second transistors in communication with at least one of the plurality of capacitors, wherein the at least one pair of second transistors produces a signal, and wherein the plurality of capacitors and the at least one pair of second transistors are connected together in an H-bridge configuration; and
    ix. a first and second power supply conduit in communication with the at least one pair of second transistors; and
  b. a Helmholtz-like magnetic coil pair in communication with the pulse generator for receiving the produced signal, wherein the Helmholtz-like magnetic coil pair is sized to generate a plurality of pulse blasts when excited by the pulse generator, wherein each pulse blast comprises a plurality of pulses, wherein the plurality of pulse blasts have a slew rate of at least 200 kiloGauss per second, and wherein the Helmholtz-like magnetic coil pair comprises:
    i. a first magnetic coil with a first magnetic coil first side and a first magnetic coil second side, wherein the first magnetic coil first side has a first polarity and the first magnetic coil second side has a second polarity, and wherein the first magnetic coil is in communication with the first power supply conduit; and
    ii. a second magnetic coil with a second magnetic coil first side and a second magnetic coil second side, wherein the second magnetic coil first side has a first polarity and the second magnetic coil second side has a second polarity, wherein the second magnetic coil is in communication with the second power supply conduit, and wherein the first magnetic coil is disposed opposite the second magnetic coil enabling the Helmholtz-like magnetic coil pair to:
    iii. treat cellular dysfunction of a tissue placed between the first and second magnetic coils; and
    iv. treat an extracellular matrix disruption of a tissue placed between the first and second magnetic coils, or combinations thereof, wherein the first magnetic coil and second magnetic coil are oriented so that when the first and second magnetic coils are energized using the pulse generator a plurality of magnetic square-wave pulses are generated for at least a duration from 0.1 microsecond to 200 microseconds without forming a sine shaped pulse wave.

17. A system for treatment of ailments, wherein the system comprises:
  a. a pulse generator comprising:
    i. a power supply;
    ii. a bi-directional communication and power port for flowing power into and out of the pulse generator and flowing communication signals into and out of the pulse generator;
    iii. a microcontroller in communication with the bi-directional communication and power port, wherein the microcontroller comprises a processor in communication with the power supply;
    iv. a data storage in communication with the processor;
    v. computer instructions with preset pulse parameters in the data storage;
    vi. at least one pair of first transistors in communication with the microcontroller;

vii. a voltage multiplier in communication with the at least one pair of first transistors, wherein the voltage multiplier comprises a plurality of diodes and a plurality of capacitors in communication with the microcontroller for increasing or decreasing a voltage of the pulse generator;
viii. at least one pair of second transistors in communication with at least one of the plurality of capacitors, wherein the at least one pair of second transistors produces a signal; and
ix. a first and second power supply conduit in communication with the at least one pair of second transistors; and b. a Helmholtz-like magnetic coil pair in communication with the pulse generator for receiving the produced signal, wherein the Helmholtz-like magnetic coil pair is sized to generate a plurality of pulse blasts when excited by the pulse generator, wherein each pulse blast comprises a plurality of pulses, wherein each pulse has a duration of longer than 200 microseconds for producing unipolar magnetic pulses with leading edge magnetic slew rates greater than 200 kiloGauss per second and trailing edge magnetic slew rates less than 200 kiloGauss per second, and wherein the Helmholtz-like magnetic coil pair comprises:
i. a first magnetic coil with a first magnetic coil first side and a first magnetic coil second side, wherein the first magnetic coil first side has a first polarity and the first magnetic coil second side has a second polarity, and wherein the first magnetic coil is in communication with the first power supply conduit; and
ii. a second magnetic coil with a second magnetic coil first side and a second magnetic coil second side, wherein the second magnetic coil first side has a first polarity and the second magnetic coil second side has a second polarity, wherein the second magnetic coil is in communication with the second power supply conduit, and wherein the first magnetic coil is disposed opposite the second magnetic coil enabling the Helmholtz-like magnetic coil pair to:
iii. treat cellular dysfunction of a tissue placed between the first and second magnetic coils; and
iv. treat an extracellular matrix disruption of a tissue placed between the first and second magnetic coils, or combinations thereof, wherein the first magnetic coil and second magnetic coil are oriented so that when the first and second magnetic coils are energized using the pulse generator a plurality of magnetic square-wave pulses are generated for at least a duration from 0.1 microsecond to 200 microseconds without forming a sine shaped pulse wave.

18. A system for treatment of ailments, wherein the system comprises:
a. a pulse generator comprising:
i. a power supply;
ii. a bi-directional communication and power port for flowing power into and out of the pulse generator and flowing communication signals into and out of the pulse generator;
iii. a microcontroller in communication with the bi-directional communication and power port, wherein the microcontroller comprises a processor in communication with the power supply;
iv. a data storage in communication with the processor;
v. computer instructions with preset pulse parameters in the data storage;
vi. at least one pair of first transistors in communication with the microcontroller;
vii. a voltage multiplier in communication with the at least one pair of first transistors, wherein the voltage multiplier comprises a plurality of diodes and a plurality of capacitors in communication with the microcontroller for increasing or decreasing a voltage of the pulse generator;
viii. at least one pair of second transistors in communication with at least one of the plurality of capacitors, wherein the at least one pair of second transistors produces a signal; and
ix. a first and second power supply conduit in communication with the at least one pair of second transistors; and b. a plurality of Helmholtz-like magnetic coil pairs, wherein the plurality of Helmholtz-like magnetic coil pairs are formed into a magnetic array with a common controller for treating a large area of tissue, wherein each Helmholtz-like magnetic coil pair is in communication with the pulse generator for receiving the produced signal, wherein each Helmholtz-like magnetic coil pair is sized to generate a plurality of pulse blasts when excited by the pulse generator, wherein each pulse blast comprises a plurality of pulses, wherein the plurality of pulse blasts have a slew rate of at least 200 kiloGauss per second, and wherein each Helmholtz-like magnetic coil pair comprises:
i. a first magnetic coil with a first magnetic coil first side and a first magnetic coil second side, wherein the first magnetic coil first side has a first polarity and the first magnetic coil second side has a second polarity, and wherein the first magnetic coil is in communication with the first power supply conduit; and
ii. a second magnetic coil with a second magnetic coil first side and a second magnetic coil second side, wherein the second magnetic coil first side has a first polarity and the second magnetic coil second side has a second polarity, wherein the second magnetic coil is in communication with the second power supply conduit, and wherein the first magnetic coil is disposed opposite the second magnetic coil enabling the plurality of Helmholtz-like magnetic coil pairs to:
iii. treat cellular dysfunction of a tissue placed between the first and second magnetic coils; and
iv. treat an extracellular matrix disruption of a tissue placed between the first and second magnetic coils, or combinations thereof, wherein the first magnetic coil and second magnetic coil are oriented so that when the first and second magnetic coils are energized using the pulse generator a plurality of magnetic square-wave pulses are generated for at least a duration from 0.1 microsecond to 200 microseconds without forming a sine shaped pulse wave.

19. The system of claim 18, wherein the magnetic array generates pulses in controlled sequences to produce a plurality of magnetic field vectors that rotate through a space proximate to the magnetic array over a preset unit of time.

20. The system of claim 18, wherein a distance between each pair of the Helmholtz-like magnetic coil pairs is adjustable to range from 0.5 inches to 10 inches.

21. The system of claim 18, wherein the magnetic array generates pulse blasts in controlled sequences to produce a plurality of magnetic field vectors that translate through space proximate the magnetic array over time.

22. The system of claim 18, wherein the plurality of Helmholtz-like magnetic coil pairs are arranged into a member selected from the group consisting of: a two-dimensional Halbach array, a one-dimensional Halbach array, or combinations thereof.

23. The system of claim 22, wherein at least one pair of the plurality of Helmholtz-like magnetic coil pairs of the Halbach array has an in-plane axis to act as a flux conduit between a normal-to-plane axis of at least one other pair of the plurality of Helmholtz-like magnetic coil pairs of the Halbach array.

24. The system of claim 23, wherein the Halbach array contains flux concentrators of iron, ferrite or a similar magnetic material to concentrate magnetic fields proximate at least one specified point within the Halbach array.

25. The system of claim 23, wherein the Halbach array is sealed within a mechanically flexible polymer coating which allows an unimpeded generation of magnetic fields.

* * * * *